United States Statutory Invention Registration [19]

[11] Reg. Number: H861

Collignon et al. [43] Published: Dec. 4, 1990

[54] METHOD FOR MANUFACTURING 3-NITRO-1,2,4-TRIAZOL-5-ONE

[75] Inventors: Steven L. Collignon, Waldorf; Robert E. Farncomb, Accokeek; Kerry L. Wagaman, Waldorf, all of Md.

[73] Assignee: The United States of America as represented by the Secretary of the Navy, Washington, D.C.

[21] Appl. No.: 210,885

[22] Filed: Jun. 23, 1988

[51] Int. Cl.[5] ..... C07D 249/14

[52] U.S. Cl. ..... 548/263.8

*Primary Examiner*—Richard D. Lovering
*Assistant Examiner*—John M. Covert
*Attorney, Agent, or Firm*—Kenneth E. Walden; Roger D. Johnson

[57] ABSTRACT

A process for preparing 3-nitro-1,2,4-triazol-5-one by nitrating 1,2,4-triazol-5-one in 70% nitric acid at a temperature of from 60° C. to 75° C. and then crystallizing out the product 3-nitro-1,2,4-triazol-5-one at a temperature of from 0° C. to 10° C. The nitro-1,2,4-triazol-5-one is useful as an explosive.

12 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR MANUFACTURING 3-NITRO-1,2,4-TRIAZOL-5-ONE

BACKGROUND OF THE INVENTION

This invention relates to heterocylic organic explosives and more particularly to nitrated triazoles.

Two methods of manufacturing 3-nitro-1,2,4-triazol-5-one (NTO) currently exist. One method used by Los Alamos National Laboratory involves adding 70% nitric acid and 1,2,4-triazol-5-one (TO) together at room temperature. The mixture is heated until the reaction begins to exotherm. The reactor is then allowed to self-heat until the reaction is complete. Yield based on the starting amount of 1,2,4-triazol-5-one is 65%. Disadvantages of this process include low yields and unsafe conditions caused by allowing the reactor to self-heat. Scale-up of this technique would be especially dangerous because of the difficulties involved in controlling the temperature and the possibility of a runaway reaction and potential fume off.

In the second prior art procedure, the French (SNPE) add 1,2,4-triazol-5-one to 98% nitric acid at 0° to 10° C. over a period of two hours. The reaction is held at this temperature for 3 hours. Water is then added to the reactor and the mixture is held for 12 hours. Disadvantages of the SNPE process are the longer reaction time, the lower yield, and the dangers associated with high acid concentrations

SUMMARY OF THE INVENTION

Accordingly, an object of this invention is to provide a new method of preparing 3-nitro-1,2,4-triazol-5-one.

Another object of this invention is to provide a new method of preparing 3-nitro-1,2,4-triazol-5-one in greater yield.

A further object of this invention is to provide a safer method of producing 3-nitro-1,2,4-triazol-5-one.

Yet another object of this invention is to provide a continuous process for producing 3-nitro-1,2,4-triazol-5-one.

This and other objects of this invention are achieved by providing:

A method of producing 3-nitro-1,2,4-triazol-5-one comprising:

(1) adding 1,2,4-triazol-5-one to 70% nitric acid at a temperature of from 60° C. to 75° C. until the molar ratio of the 1,2,4-triazole-5-one added to the nitric acid is from 1:8 to 1:4;

(2) holding the mixture formed in step (1) at a temperature of from 60° C. to 75° C. until the 1,2,4-triazol-5-one has been nitrated to form 3-nitro-1,2,4-triazol-5-one;

(3) cooling the mixture formed in step (2) to a temperature of from 0° C. to 10° C. to crystallize out the 3-nitro-1,2,4-triazol-5-one; and (4) isolating the product 3-nitro-1,2,4-triazol-5-one.

DETAILED DESCRIPTION OF THE PREFERRED EMBODIMENT

This invention may be used either as a batch or as a continuous process to form 3-nitro-1,2,4-triazol-5-one (NTO) from 1,2,4-triazol-5-one (TO) by nitration. In the batch process, 70 percent nitric acid is heated to a temperature in the range of from 60° to 75° C., preferably from 65° C. to 70° C. Then 1,2,4-triazol-5-one is added slowly to maintain the reaction temperature in the range of from 60° C. to 75° C., preferably from 65° C. to 70° C., until the molar ratio of the 1,2,4-triazol-5-one added to the nitric acid present is from 1:8 to 1:4, preferably from 1:7 to 1:5, and more preferably about 1:6. This addition will generally take from about 1 to 2 hours. After the addition is completed the temperature of the reaction mixture is maintained at 60° C. to 75° C., preferably from 65° C. to 70° C., for about an additional hour to insure completion of the nitration reaction.

The reaction batch is then cooled to a temperature of from 0° C. to 10° C. to cause the product 3-nitro-1,2,4-triazol-5-one to crystallize out. The 3-nitro-1,2,4-triazol-5-one is then separated (e.g., filtered) from the solution.

The process may also be run as a continuous process. As in the batch process, 70 percent nitric acid is heated in the reactor to a temperature in the range of from 60° C. to 75° C., preferably from 65° C. to 70° C. Then 1,2,4-triazol-5-one is added slowly to maintain the reaction temperature in the range of from 60° C. to 75° C., preferably from 65° C. to 70° C., until the molar ratio of the 1,2,4-triazol-5-one added to the nitric acid is from 1:8 to 1:4, preferably from 1:7 to 1:5, and more preferaby about 1:6. Once the reactor is charged in this manner, 1,2,4-triazol-5-one and 70% nitric acid are continuously added to the reactor in the same molar ratio as was used to charge it. This may be done as a feed solution of 1,2,4-triazol-5-one dissolved in the nitric acid. However, there is a danger of "fume off" occurring while the 1,2,4-triazol-5-one is being dissolved in the 70% nitric acid. Therefore, the 1,2,4-triazol-5-one and nitric acid are preferably added as separate feeds with a dry solids feeder being used to add the 1,2,4-triazol-5-one. At the same time, a product stream is drawn from the reactor at a rate of flow equal to the rate of flow of the feed solution. The rate of flow is adjusted to cause a complete turn over or change of the reactor contents every 2 to 10 hours. During the process the reaction mixture is maintained at a temperature of from 60° C. to 75° C., preferably from 65° C. to 70° C.

The product stream from the reactor is cooled down to from 0° C. to 10° C. and the product crystals of 3-nitro-1,2,4-triazol-5-one are then separated (e.g., filtered) from the acid solution.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE 1

Batch Process

In a 12 liter flask 6.67 L of 70% nitric acid was heated to 65° C. With agitation, 1.484 kg of 1,2,4-triazol-5-one was added stepwise over a period of about 1.0 hour to the preheated nitric acid. The reaction temperature was maintained between 65° C. and 70° C. for an additional hour. The 3-nitro-1,2,4-triazol-5-one product and acid mixture was cooled to 10° C. and filtered. The yield based on the starting amount of 1,2,4-triazol-5-one was 90%.

EXAMPLE 2

Continuous Process

In a 12 liter flask (reactor) 6.67 L of 70% nitric acid was heated to 65°–70° C. With agitation, 1.484 kg of 1,2,4-triazol-5-one was added stepwise over a period of 1.0 to 1.5 hours. Nitric acid, 70%, was pumped into the reactor at a rate of 6.672 liters/four hours and 1.484kg 1,2,4-triazol-5-one was also added over a four hour period using a dry solids feeder. The temperature of the mixture in the reactor was maintained at 65°–70° C. An equal flow rate was pumped from the reactor to a crystallizer where the nitric acid and 3-nitro-1,2,4-triazol-5-one mixture was cooled down to 10° C. and then pumped through a filter. After filtering, the product 3-nitro-1,2,4-triazol-5-one was dried and weighed, the yield based on the starting amount of 1,2,4-triazol-5-one was 83%.

Obviously, numerous modifications and variations of the present invention are possible in light of the above teachings. It is therefore to be understood that within the scope of the appended claims the invention may be practiced otherwise than as specifically described herein.

What is claimed is:

1. A process for producing 3-nitro-1,2,4-triazol-5-one comprising (1) adding 1,2,4-triazol-5-one to 70% nitric acid at a temperature of from 60° C. to 75° C. until the molar ratio of the 1,2,4-triazol-5-one added to the nitric acid is from 1:8 to 1:4;

(2) holding the mixture formed in step (1) at a temperature of from 60° C. to 75° C. until the 1,2,4-triazol-5-one has been nitrated to form 3-nitro-1,2,4-triazol-5-one;

(3) cooling the mixture formed in step (2) to a temperature of from 0° C. to 10° C. to crystallize out the 3-nitro-1,2,4-triazol-5-one; and (4) isolating the product 3-nitro-1,2,4-triazol-5-one.

2. The process of claim 1 wherein the mixtures in steps (1) and (2) are agitated.

3. The process of claim 1 wherein the molar ratio of 1,2,4-triazol-5-one to nitric acid is from 1:7 to 1:5.

4. The process of claim 3 wherein the molar ratio of 1,2,4-triazol-5-one to nitric acid is about 1:6.

5. The process of claim 1 wherein the temperature used in steps (1) and (2) is from 65° C. to 70° C.

6. A continuous process for producing 3-nitro-1,2,4-triazol-5-one comprising (1) charging a reactor by adding 1,2,4-triazol-5-one to 70% nitric acid at a temperature of from 60° C. to 75° C. until the molar ratio of the 1,2,4-triazol-5-one added to the nitric acid is from 1:8 to 1:4;

(2) continuously feeding 1,2,4-triazol-5-one and nitric acid into the reactor in the same molar ratio as was used to charge the reactor in step (1) while maintaining the reactor temperature in the range of from 60° C. to 75° C.;

(3) continuously drawing off a product stream from the reactor;

(4) cooling the product stream to from 0° C. to 10° C. to crystallize out the product 3-nitro-1,2,4-triazol-5-one; and (5) isolating the product 3-nitro-1,2,4-triazol-5-one; provided that the rates of flow of the feed and the product streams are adjusted to completely change the contents of the reactor every 2 to 10 hours.

7. The process of claim 6 wherein the reaction mixture is agitated.

8. The process of claim 6 wherein the molar ratio of 1,2,4-triazol-5-one to nitric acid is from 1:7 to 1:5.

9. The process of claim 8 wherein the molar ratio of 1,2,4-triazol-5-one to nitric acid is about 1:6.

10. The process of claim 6 wherein the temperature used in steps (1) and (2) is in the range of from 65° C. to 70° C.

11. The process of claim 6 wherein in step (2) the nitric acid and the 1,2,4-triazol-5-one are fed in separately.

12. The process of claim 6 wherein the rates of flow of the feed and the product streams are adjusted to completely change the contents of the reactor every 2 to 6 hours.

* * * * *